(12) United States Patent
Bosman et al.

(10) Patent No.: US 9,012,627 B2
(45) Date of Patent: Apr. 21, 2015

(54) METHOD TO PRODUCE URETONIMINE-MODIFIED ISOCYANATE COMPOSITION

(75) Inventors: Joris Karel Peter Bosman, Herselt (BE); Nicole Mangelschots, Wilsele (BE)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 13/637,037

(22) PCT Filed: Mar. 2, 2011

(86) PCT No.: PCT/EP2011/053080
§ 371 (c)(1),
(2), (4) Date: Sep. 25, 2012

(87) PCT Pub. No.: WO2011/120750
PCT Pub. Date: Oct. 6, 2011

(65) Prior Publication Data
US 2013/0012698 A1    Jan. 10, 2013

(30) Foreign Application Priority Data
Mar. 30, 2010 (EP) .................................. 10 158308

(51) Int. Cl.
*C07D 229/00* (2006.01)

(52) U.S. Cl.
CPC .................................... *C07D 229/00* (2013.01)

(58) Field of Classification Search
CPC ..................................................... C07D 229/00
USPC ....................................................... 504/202
See application file for complete search history.

(56) References Cited

U.S. PATENT DOCUMENTS

| 4,014,935 A | 3/1977 | Ibbotson |
| 4,088,665 A | 5/1978 | Findeisen et al. |
| 4,424,288 A | 1/1984 | Patton et al. |
| 4,743,626 A | 5/1988 | Narayan |
| 4,937,012 A | 6/1990 | Kan et al. |
| 5,300,545 A * | 4/1994 | Kazmierczak et al. ....... 524/102 |
| 6,120,699 A | 9/2000 | Narayan et al. |
| 6,489,503 B1 | 12/2002 | Narayan et al. |
| 7,030,274 B2 | 4/2006 | Rosthauser et al. |
| 7,745,659 B2 | 6/2010 | Wershofen et al. |
| 7,790,907 B2 | 9/2010 | Savino et al. |
| 8,022,200 B2 | 9/2011 | Wershofen et al. |
| 2006/0128928 A1 * | 6/2006 | Wershofen et al. ............. 528/49 |
| 2007/0155937 A1 * | 7/2007 | Wershofen et al. ............. 528/44 |
| 2008/0021176 A1 * | 1/2008 | Savino et al. ................. 525/453 |
| 2008/0085987 A1 | 4/2008 | Savino et al. |
| 2008/0200619 A1 | 8/2008 | Bosman |
| 2009/0143542 A1 | 6/2009 | Savino et al. |

FOREIGN PATENT DOCUMENTS

| EP | 032 011 A | 7/1981 |
| EP | 189 156 A | 7/1986 |
| EP | 193 787 A | 9/1986 |
| EP | 308 710 A | 3/1989 |
| EP | 1 616 858 A | 1/2006 |
| EP | 1 671 988 A | 6/2006 |
| WO | WO 2007/006622 A | 1/2007 |
| WO | WO 2008/009669 A | 1/2008 |
| WO | WO 2008/040722 A | 4/2008 |

* cited by examiner

*Primary Examiner* — Golam M M Shameem
*Assistant Examiner* — Laura Daniel
(74) *Attorney, Agent, or Firm* — Robert A. Diaz

(57) ABSTRACT

A method to produce uretonimine-modified isocyanate composition comprises

Providing an organic isocyanate composition having two or more isocyanate groups;

Reacting, in the presence of a suitable catalyst, said polyisocyanate composition to form uretonimine-modified isocyanate composition comprising carbodiimide groups and uretonimine groups;

terminating said reacting by the addition of an amount of oxalic acid mono alkyl ester halide.

9 Claims, No Drawings

METHOD TO PRODUCE URETONIMINE-MODIFIED ISOCYANATE COMPOSITION

CROSS-REFERENCE TO RELATED APPLICATIONS

This application is the National Phase of International Application PCT/EP2011/053080 filed Mar. 2, 2011 which designated the U.S. and which claims priority to European App. Serial No. 10158308.6 filed Mar. 30, 2010. The noted applications are incorporated herein by reference.

BACKGROUND OF THE INVENTION

1. Field of the Invention

The present invention relates to processes to provide uretonimine-modified isocyanate composition and to uretonimine-modified isocyanate composition.

2. Background Information

Organic isocyanate compositions are well known in the art. Several compositions, in particular the ones comprising methyl diphenylisocyanate isomers (MDI isomers), and most in particular the MDI compositions comprising a high amount of 4,4'MDI, are solid. To provide liquid compositions, typically the composition is modified by introducing uretonimine-groups, this is done by reacting all or part of the organic isocyanate composition over a catalyst, whereby first carbodiimide groups are proved, which on their turn further react with isocyanate groups to provide uretonimine groups. This reaction must be terminated by the addition of so-called catalyst killers, quenching agents or stopping agents.

Typically, acid chlorides are mentioned as catalyst stoppers in EP 0193787, EP 0189156, EP 0308710, U.S. Pat. No. 7,030,274, U.S. Pat. No. 6,120,699, U.S. Pat. No. 4,424,288 and U.S. Pat. No. 4,088,665. In WO 2008/040722 and U.S. Pat. No. 6,489,503, a backblending process is described wherein the catalyst killer being oxalylchloride is mentioned.

In U.S. Pat. No. 4,014,935, the addition of PC15 as catalyst stopper results in a water clear liquid. PC15 is a powder which is very toxic and difficult to handle.

In EP32011A1, carbodiimine-modified isocyanate is provided by reacting the isocyanate composition over a catalyst, whereby carbodiimide groups and uretonimine groups are proved. These two components form part in a reversible reaction of

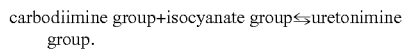

The catalyst used to provide the carbodiimine groups is stopped by the addition of a catalyst killer, in particular thionyl chloride. The equilibrium reaction is forced to the carbodiimine side (i.e. the amount of uretonimine groups is reduced) by reacting carbodiimine groups with a diester of an aliphatic dicarboxylic acid in the presence of oxalic or formic acid. Carbodiimine groups having reacted with the diester, does not form part anymore in the equilibrium reaction. The amount of uretonimine in the isocyanate can be brought to substantially zero.

In WO2008/009669, the use of oxalyl chloride as catalyst quencher is suggested. This catalyst quenching or killing agent is toxic and had a boiling point of about 63 deg C. as the quenching typically is to be done at temperatures of about 80 to 110 deg C., oxalyl chloride is difficult to handle.

WO2007/006622 suggests the use of adipoylchloride as catalyst killing agent. It was also noticed that uretonimine modified isocyanates wherein adipoyl chloride was used as catalyst killer, may become less stable, i.e. the catalyst still in the composition, may regain part of its activity. This can cause the creation of $CO_2$ in the stored isocyanate containers, and may cause a potential safety risk when opening the containers.

It is an object of the present invention to provide an alternative method to provide uretonimine-modified isocyanate composition, which overcomes, at least partially, some or all drawbacks of prior art. Embodiments of the present invention provide uretonimine-modified isocyanate composition which are water clear, using less or even non toxic catalyst killers, while providing a stable product.

The above objective is accomplished by a method according to the present invention.

SUMMARY OF THE INVENTION

According to a first aspect of the present invention, a method to produce uretonimine-modified isocyanate composition is provided, the method comprises
  Providing an organic isocyanate composition having two or more isocyanate groups;
  Reacting, in the presence of a suitable catalyst, said polyisocyanate composition to form uretonimine-modified isocyanate composition comprising carbodiimide groups and uretonimine groups;
  terminating said reacting by the addition of an amount of oxalic acid mono alkyl ester halide.

DETAILED DESCRIPTION OF THE INVENTION

It is understood that terminating the reaction means the termination of the catalytic reaction to form carbodiimide groups and uretonimine groups. Therefore, according to a first aspect of the present invention, the method to produce uretonimine-modified isocyanate comprises
  Providing an organic isocyanate composition having two or more isocyanate groups;
  Reacting, in the presence of a suitable catalyst, said polyisocyanate composition to form uretonimine-modified isocyanate composition comprising carbodiimide groups and uretonimine groups;
  Deactivating the catalyst by the addition of an amount of oxalic acid mono alkyl ester halide.

The oxalic acid mono alkyl ester halide added in fact acts as a killing agent for the catalyst. It is understood that the amount of oxalic acid mono alkyl ester halide needs to be sufficient to kill all the present catalyst, in order to terminate the reaction.

The termination by killing the catalyst using oxalic acid mono alkyl ester halide result in the provision of an uretonimine-modified isocyanate composition comprising at least traces of the oxalic acid mono alkyl ester halide used. The oxalic acid mono alkyl ester halide used may be present in a molar ratio of 3 to 300 of oxalic acid mono alkyl ester halide per mole catalyst.

Preferably the organic isocyanate composition is a polyisocyanate composition.

The use of oxalic acid mono alkyl ester halide has several advantages.

A water clear uretonimine-modified isocyanate composition may be obtained, having a yellowness index in the range of 1 to 10, preferably in the range of 1 to 7, most preferably in the range of 1 to 5. The method according to the invention has the additional advantage that the color of the obtained uretonimine-modified isocyanate composition does not substantially change over time.

The yellowness index is measured by at ambient temperature, i.e. at 20 deg C., using ASTM D1925 measured with a Hunterlab Ultrascan PRO using a 20 mm cell.

Additional to the benefit as far as colour of the uretonimine-modified isocyanate composition is concerned, the use of oxalic acid mono alkyl ester halide has as an advantage that the uretonimine-modified isocyanate composition obtained is more stable over time, and that the oxalic acid mono alkyl ester halide is not considered toxic, has a boiling point close to or above the typical reaction temperatures used and is fairly easy to handle.

In order to have best results as far as color of the uretonimine-modified isocyanate composition is concerned, the polyisocyanate composition to be modified preferably has a Yellowness Index of less than or equal to 4.

The advantage is also that the use of thionyl chloride can be avoided. The latter component is known to cause the isocyanate to have a yellowish color.

Hence according to some embodiments, the termination of the catalytic reaction to form carbodiimide groups and uretonimine groups can be done without the use of thionyl chloride. Even more the use of thionyl chloride can be completely avoided.

It is further an advantage that the use of toxic products such as oxalyl chloride can be avoided. Hence according to some embodiments, the termination of the catalytic reaction to form carbodiimide groups and uretonimine groups can be done without the use of oxalyl chloride.

According to some embodiments, the oxalic acid mono alkyl ester halide may be ethyl oxalyl chloride or methyl oxalyl chloride.

According to some embodiments, the molar ratio oxalic acid mono alkyl ester halide over catalyst may be in the range of 15 to 150 of oxalic acid mono alkyl ester halide per mole catalyst.

Preferably the mole ratio oxalic acid mono alkyl ester halide over catalyst is in the range of a molar ratio of 15 to 150 of oxalic acid mono alkyl ester halide per mole catalyst, most preferred in the range of 25 to 100.

Various types of catalysts can be used. Suitable types of catalyst are listed in U.S. Pat. No. 6,489,503B1. Preferably phospholene oxide- or phospholene sulfide-type catalysts are used, having the generic formulae.

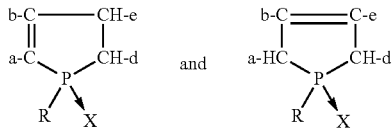

wherein a, b, c and d are each selected from the group consisting of hydrogen and hydrocarbyl from 1 to 12 carbon atoms inclusive, R is selected from the group consisting of lower alkyl and aryl and X is selected from the group consisting of oxygen and sulfur. Representative compounds are 1-phenyl-2-phospholene-1-oxide; 3-methyl-1-phenyl-2-phospholene-1-oxide; 1-phenyl-2-phospholene-1-sulfide; 1-methyl-2-phospholene-1-oxide; 1-methyl-3-methyl-2-phospholene-1-oxide; 1-phenyl-2-phospholene-1-1 sulfide; 1-ethyl-2-phospholene-1-oxide; 1-ethyl-3-methyl-2-phospholene-1-oxide; 1-ethyl-3-methyl-2-phospholene-1-sulfide; and the isomeric phospholenes corresponding to the above named compounds and mixtures thereof.

According to some embodiments, the catalyst may be phospholene oxide.

Preferred catalysts are 3-methyl-1-phenyl-3-phospholene-1-oxide, 3-methyl-1-phenyl-2-phospholene-1-oxide, 1-methyl-3-phospholene-1-oxide, 1-methyl-2-phospholene-1-oxide, 1-ethyl-3-phospholene-1-oxide, 1-ethyl-2-phospholene-1-oxide 1-phenyl-3-phospholene-1-oxide, and 1-phenyl-2-phospholene-1-oxide. Most preferred are 3-methyl-1-phenyl-3-phospholene-1-oxide, 3-methyl-1-phenyl-2-phospholene-1-oxide and mixtures of these isomers.

According to some embodiments, the catalyst may be present in the polyisocyanate composition in a concentration of 0.5 to 50 ppm.

Preferably the catalyst is present in the polyisocyanate composition in a concentration of 1 to 20 ppm, most preferred in a concentration of 2 to 12 ppm.

The uretonimine may be formed as described above from polyisocyanate compositions including methyl diphenylisocyanate (also referred to as MDI), such as 4,4'MDI and/or 2,4'-MDI and/or 2,2'-MDI isomers and mixtures thereof (particularly those comprising at least about 45 weight percent 4,4'-MDI), as well as aromatic, aliphatic and cycloaliphatic polyisocyanates and combinations thereof. Representative of these types are monoisocyanates including phenyl isocyanates, cyclohexyl isocyanate; the diisocyanates such as m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, hexahydrotoluene diisocyanate (and isomers), isophorone diisocyanate, hydrogenated methylene bis(phenylisocyanate), naphthalene-1,5 diisocyanate, 1-methoxyphenyl-2,4-diisocyanate, 4,4'-biphenylene diisocyanate, 3,3'-dimethoxy-4,4'-biphenyl diisocyanate, 3,3'-dimethyldiphenylmethane-4,4'-diisocyanate; the triisocyanate such as 4,4',4"-triphenylmethane triisocyanate and toluene 2,4,6-triisocyanate; and the tetraisocyanates such as 4,4'-dimethyldiphenylmethane-2,2',5,5'-tetraisocyanate and polymeric polyisocyanates such as polymethylene polyphenylene polyisocyanate, by way of non-limiting example. The reaction mechanism in each case is well known to those skilled in the art.

According to some embodiments, the polyisocyanate composition may comprise 4,4'MDI and/or 2,4'-MDI and/or 2,2'-MDI isomers and mixtures thereof.

Preferably the 4,4'MDi content is 50 to 100% wt.

Possibly the polyisocyanate composition consists of 4,4'MDI, or consists of a blend of 4,4'MDI with 2,4'-MDI and/or 2,2'-MDI. The term "consist" is to be understood as will the composition contains, next to the species summed, optionally some typical impurities at typical impurity levels.

In addition to the components as set out above, the uretonimine-modified isocyanate composition may further comprise stabilizers (sometimes referred to as anti-oxidants), preferably primary anti-oxidants of the phenolic type such as BHT, Irganox 1076, Irganox 1010, Irganox 1135, Anox 1315, Ralox 926, Isonox 132 and secondary anti-oxidants quite often providing a synergistic effect with the phenolic anti-oxidants such as thioethers, phosphorous acid esters, comprising aliphatic, aromatic or mixed aliphatic and aromatic groups such as triethylphosphite triphenylphospite, Doverphos 7 and the like and sterically hindered amines such as secondary phenylamines like Irganox 5057, and most preferred a combination of these two. Multifunctional anti-oxidants combining primary and secondary anti-oxidants in one molecule are possible as well. Representative examples are Irganox 1726 and Irganox 1520, also known as thiosynergists.

According to some embodiments, the polyisocyanate composition further may comprise a first stabilizer of the type of sterically hindered phenols and a second stabilizer of the type of phosphorous acid esters or sterically hindered amines or thioethers or multifunctional anti-oxidants.

Reaction temperature during the reacting, in the presence of a suitable catalyst, said polyisocyanate composition to form uretonimine-modified isocyanate composition comprising carbodiimide groups and uretonimine groups, is preferably in the range of 80 to 130 deg C., more preferred in the range of 90 to 120 deg C.

According to a second aspect of the present invention, the method to produce uretonimine-modified isocyanate composition may further comprise the addition of organic isocyanate composition, e.g. polyisocyanate composition to the already obtained uretonimine-modified isocyanate composition.

As an example, the method may comprise the provision of a volume or stream of an organic isocyanate composition, e.g. a polyisocyanate composition, which is separated in two distinct volumes or streams. One of the volumes or streams is subjected to the steps as set out in relation to the first aspect of the present invention to provide an uretonimine-modified isocyanate composition, the other is not modified. The method according to the second aspect of the present invention further has the step of blending the two volumes or streams again to provide an uretonimine-modified isocyanate composition.

Hence according to this second aspect of the present invention, the method according to the first aspect of the present invention further comprises the step of adding unmodified organic isocyanate composition after termination of the reaction by adding an amount of oxalic acid mono alkyl ester halide.

The adding of unmodified organic isocyanate composition may be done after the catalyst is killed, or simultaneously with the addition of the catalyst killer, or even before the addition of the catalyst killer being oxalic acid mono alkyl ester halide.

Optionally, the addition of the catalyst killer being oxalic acid mono alkyl ester halide, is done in subsequent small amounts. Also the addition of the unmodified organic isocyanate composition may be done in consecutive additions, optionally alternating with addition of catalyst killer being oxalic acid mono alkyl ester halide.

Typically the organic isocyanate compound used for modifying according to the first aspect of the present invention, and the organic isocyanate compound used for blending with the uretonimine-modified isocyanate composition is the same. Typically a blend ratio of above 0 to and including 10, e.g. above 0 to and including 5, such as above 0 to and including 1, e.g. in the range of 0.000001 to 10, e.g. from 0.000001 to 5, such as from of 0.000001 to 1, expressed as weight of the non modified organic isocyanate compound used to provide the blend over the weight of the uretonimine-modified isocyanate composition used to provide this blend.

The termination by killing the catalyst using oxalic acid mono alkyl ester halide, and further blending the modified isocyanate compound with non-modified organic isocyanate compounds, result in the provision of an uretonimine-modified isocyanate composition comprising at least traces of the oxalic acid mono alkyl ester halide used. The oxalic acid mono alkyl ester halide used may be present in an amount of a molar ratio of 3 to 300 of oxalic acid mono alkyl ester halide per mole catalyst.

According to a third aspect of the present invention, uretonimine-modified isocyanate composition is provided, which composition is obtainable by one of the methods as set out in any one of the methods according to the first or second aspect of the invention.

According to a further aspect of the present invention, uretonimine-modified isocyanate composition is provided, which composition comprises uretonimine, carbodiimide and oxalic acid mono alkyl ester halide.

The products obtainable may have an NCO value typically in the range of 25 to 32.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

When reference is made to % wt, % w or percentage by weight of a component, this term expresses the ratio of the weight of the specific component over the weight of the composition in which it is present, expressed as percentage.

EXAMPLES

Comparative Example 1

650 parts of a mixture of about 98% of 4,4'- and 2.0% 2,4'-isomers of methylene(phenylisocyanate) containing 1500 ppm 11076 are mixed with 0.0033 parts of 3-methyl-1-phenyl-2-phospholene-1-oxide and heated to 110° C. and maintained at that temperature to reach the target NCO value 27.5 wt %. The reaction contents are than cooled to 80° C. by adding 100 parts of a mixture of about 98% of 4,4'- and 2.0% 2,4'-isomers of methylene(phenylisocyanate). 0.088 parts thionyl chloride are added and stirred for 1 hour at 70° C. After 1 hour 350 parts of a mixture of about 98% of 4,4'- and 2.0% 2,4'-isomers of methylene(phenylisocyanate) and 0.55 parts triphenyl phosphite is added.

End product is a light yellow liquid, YI 13.82, NCO value 29.5 wt %.

Comparative Example 2

650 parts of a mixture of about 98% of 4,4'- and 2.0% 2,4'-isomers of methylene(phenylisocyanate) containing 1500 ppm 11076 are mixed with 0.0033 parts of 3-methyl-1-phenyl-2-phospholene-1-oxide and heated to 110° C. and maintained at that temperature to reach the target NCO value 27.5 wt %. The reaction contents are than cooled to 105° C. and 0.275 parts adipoyl chloride are added. 100 parts of a mixture of about 98% of 4,4'- and 2.0% 2,4'-isomers of methylene(phenylisocyanate) are added and stirred for 1 hour at 70° C. After 1 hour 350 parts of a mixture of about 98% of 4,4'- and 2.0% 2,4'-isomers of methylene(phenylisocyanate) and 0.55 parts triphenyl phosphite is added.

End product is a water clear liquid, YI 4.22, NCO value 29.5 wt %.

Example 3

650 parts of a mixture of about 98% of 4,4'- and 2.0% 2,4'-isomers of methylene(phenylisocyanate) containing 1500 ppm 11076 are mixed with 0.0033 parts of 3-methyl-1-phenyl-2-phospholene-1-oxide and heated to 110° C. and maintained at that temperature to reach the target NCO value 27.5 wt %. The reaction contents are than cooled to 80° C. 0.066 parts methyl oxalyl chloride are added and stirred for 1 hour at 70° C. After 1 hour 450 parts of a mixture of about 98% of 4,4'- and 2.0% 2,4'-isomers of methylene(phenylisocyanate) and 0.55 parts triphenyl phosphite is added.

End product is a water clear liquid, YI 4.08, NCO value 29.5 wt %.

Example 4

650 parts of a mixture of about 98% of 4,4'- and 2.0% 2,4'-isomers of methylene(phenylisocyanate) containing 1500 ppm Irganox 1076 are mixed with 0.0033 parts of 3-methyl-1-phenyl-2-phospholene-1-oxide and heated to 110° C. and maintained at that temperature to reach the target NCO value 27.5 wt %. The reaction is stopped at 110° C. with 0.11 parts ethyl oxalyl chloride. The reaction contents are then cooled by adding 100 parts of a mixture of about 98% of 4,4'- and 2.0% 2,4'-isomers of methylene(phenylisocyanate) and stirred for 1 hour at 70° C. After 1 hour 350 parts of a mixture of about 98% of 4,4'- and 2.0% 2,4'-isomers of methylene (phenylisocyanate) and 0.55 parts triphenyl phosphite is added.

End product is a water clear liquid, YI 3.56, NCO value 29.5 wt %.

To measure the storage stability the products are stored for 4 days at 80° C. A comparison of viscosity, Yellowness index and NCO value between freshly obtained composition and the composition stored at 80 deg C. for 4 days is shown in table I.

TABLE I

| | YI fresh | YI after 4 days at 80 deg. C. | NCO value decrease after 4 days at 80 deg C. (%) | viscosity increase after 4 days at 80 deg C. (cP) |
|---|---|---|---|---|
| Comp ex 1 | 13.82 | 19.32 | 0.6 | 15 |
| Comp ex 2 | 4.22 | 25.72 | 0.9 | 29 |
| Example 3 | 4.08 | 6.58 | 0.5 | 9 |
| Example 4 | 3.56 | 9.66 | 0.4 | 7 |

The use of thionyl chloride (comparative example 1) show already a yellowish fresh product.

The use of adipoyl chloride looses its catalyst deactivating capability, resulting not only in the YI to increase during forced aging (YI increase from 4.22 to 25.72), but clearly shows a viscosity increase of 29 cP.

This viscosity increase is due to the creation of carbodiimide groups and uretonimine groups, caused by the catalyst to regain at least part of its activity. During the creation of a carbodiimide group by reaction of two isocyanate groups, $CO_2$ is released. When the uretonimine-modified isocyanate composition is stored in air- and watertight containers, this $CO_2$ release can cause a pressure build up inside the container.

It is to be understood that although preferred embodiments and/or materials have been discussed for providing embodiments according to the present invention, various modifications or changes may be made without departing from the scope and spirit of this invention.

The invention claimed is:

1. A method to produce uretonimine-modified isocyanate composition having a yellowness index in the range of 1 to 10 after four days at 80° C. without the use of oxalyl chloride, the method comprising:
    Providing a first organic isocyanate composition having two or more isocyanate groups;
    Reacting, in the presence of a suitable catalyst, said polyisocyanate composition to form uretonimine-modified isocyanate composition comprising carbodiimide groups and uretonimine groups; and
    Deactivating the catalyst by the addition of an amount of an oxalic acid mono alkyl ester halide, wherein said oxalic acid mono alkyl ester halide is selected from the group consisting of ethyl oxalyl chloride or methyl oxalyl chloride.

2. A method according to claim 1, wherein the molar ratio oxalic acid mono alkyl ester halide over catalyst is in the range of 15 to 150 of oxalic acid mono alkyl ester halide per mole catalyst.

3. A method according to claim 1, wherein the catalyst is phospholene oxide.

4. A method according to claim 1, wherein the catalyst is present in the polyisocyanate composition in a concentration of 0.5 to 50 ppm.

5. A method according to claim 1, wherein said polyisocyanate composition further comprises a first stabilizer of the type of sterically hindered phenols and a second stabilizer of the type of phosphorous acid esters or sterically hindered amines or thioethers or multifunctional anti-oxidants.

6. A method according to claim 1, wherein the method further comprises the step of adding unmodified organic isocyanate composition after termination of the reaction by adding an amount of oxalic acid mono alkyl ester halide.

7. The method according to claim 1, wherein the method further comprises adding a second organic isocyanate composition comprising the reaction product of the first organic isocyanate composition and the catalyst to form the uretonimine-modified isocyanate composition; and wherein the uretonimine-modified isocyanate composition after four days at 80° C. has a viscosity increase of 9 cP.

8. The method according to claim 1, wherein the method further comprises adding a second organic isocyanate composition comprising the reaction product of the first organic isocyanate composition and the catalyst to form the uretonimine-modified isocyanate composition; and wherein the uretonimine-modified isocyanate composition after four days at 80° C. has a viscosity increase of 7 cP.

9. A method to produce uretonimine-modified isocyanate composition having a yellowness index in the range of 1 to 10 after four days at 80° C. without the use of oxalyl chloride, the method comprising:
    Providing a first organic isocyanate composition having two or more isocyanate groups;

Reacting, in the presence of a suitable catalyst, said polyisocyanate composition to form uretonimine-modified isocyanate composition comprising carbodiimide groups and uretonimine groups; and Deactivating the catalyst by the addition of an amount of a deactivating compound consisting of an oxalic acid mono alkyl ester halide, wherein said oxalic acid mono alkyl ester halide is selected from the group consisting of ethyl oxalyl chloride or methyl oxalyl chloride; and wherein the oxalic acid mono alkyl ester halide is the only deactivating compound added to the composition.

* * * * *